(12) United States Patent
Nanni et al.

(10) Patent No.: US 7,515,683 B2
(45) Date of Patent: Apr. 7, 2009

(54) UNIT FOR ACQUIRING DENTAL RADIOGRAPHIC IMAGES

(75) Inventors: Eros Nanni, Castel Guelfo di Bologna (IT); Stefano Malucelli, Cannuzzo di Cervia (IT); Dario Righini, Imola (IT); Luciano Langella, Casnate (IT)

(73) Assignee: CEFLA Società Cooperativa, Imola (IT)

( * ) Notice: Subject to any disclaimer, the term of this patent is extended or adjusted under 35 U.S.C. 154(b) by 0 days.

(21) Appl. No.: 11/604,641

(22) Filed: Nov. 27, 2006

(65) Prior Publication Data

US 2007/0237291 A1    Oct. 11, 2007

(30) Foreign Application Priority Data

Nov. 28, 2005   (EP) .................................. 05425838

(51) Int. Cl.
*A61B 6/14* (2006.01)
*H05G 1/02* (2006.01)

(52) U.S. Cl. ........................................ 378/38; 378/193

(58) Field of Classification Search ......... 378/193–198, 378/208
See application file for complete search history.

(56) References Cited

U.S. PATENT DOCUMENTS

| 1,870,959 | A | * | 8/1932 | Morrison ..................... 378/201 |
| 3,033,628 | A | * | 5/1962 | Hoffman ..................... 211/117 |
| 3,045,118 | A | * | 7/1962 | Hollman et al. ............... 378/39 |
| 5,069,433 | A | | 12/1991 | Womack et al. |
| 5,553,115 | A | | 9/1996 | Odaka et al. |
| 6,302,581 | B1 | * | 10/2001 | Sliski et al. ................. 378/198 |
| 2004/0228449 | A1 | | 11/2004 | Hubner et al. |

FOREIGN PATENT DOCUMENTS

| DE | 7584454 | 8/1951 |
| DE | 4239825 | 3/1994 |
| DE | 4333913 | 4/1994 |
| DE | 19638388 | 4/1998 |
| DE | 10215987 | 11/2003 |
| DE | 10215988 | 12/2003 |

* cited by examiner

*Primary Examiner*—Irakli Kiknadze
(74) *Attorney, Agent, or Firm*—Lieberman & Brandsdorfer, LLC

(57) ABSTRACT

A unit for acquiring dental radiographic images of a patient is provided with an x-ray head coupled to a respective supporting arm via a ball joint.

3 Claims, 3 Drawing Sheets

UNIT FOR ACQUIRING DENTAL RADIOGRAPHIC IMAGES

The present invention relates to a unit for acquiring dental radiographic images.

BACKGROUND OF THE INVENTION

In the dentistry sector, a unit for acquiring dental radiographic images of the type comprising an x-ray head for outputting x-rays, a supporting arm of the x-ray head, and means for coupling the x-ray head to the supporting arm itself is known.

Generally, the coupling means comprise a connecting bracket hinged to the x-ray head and to the supporting arm by means of two cylindrical joints to turn, with respect to the x-ray head and to the supporting arm themselves, about respective fulcrum axes substantially transversal to each other.

The known units for acquiring dental radiographic images of the type described above present some drawbacks mainly deriving from the fact the cylindrical joints coupling the supporting bracket to the x-ray head and the supporting arm ensure a relatively low movement capacity of the x-ray head.

The known units for acquiring dental radiographic images of the type described above also present the further drawback in that the connection bracket and the two cylindrical coupling joints make the unit itself relatively heavy and cumbersome.

SUMMARY OF THE INVENTION

It is the object of the present invention to provide a unit for acquiring dental radiographic images which is free from the drawbacks explained above and which is simple and cost-effective to make.

According to the present invention, a unit for acquiring dental radiographic images as claimed in the attached claims is provided.

BRIEF DESCRIPTION OF THE DRAWINGS

The present invention will now be described with reference to the accompanying drawings illustrating a non-limitative embodiment example thereof, in which.

DETAILED DESCRIPTION OF THE INVENTION

Figure 1:
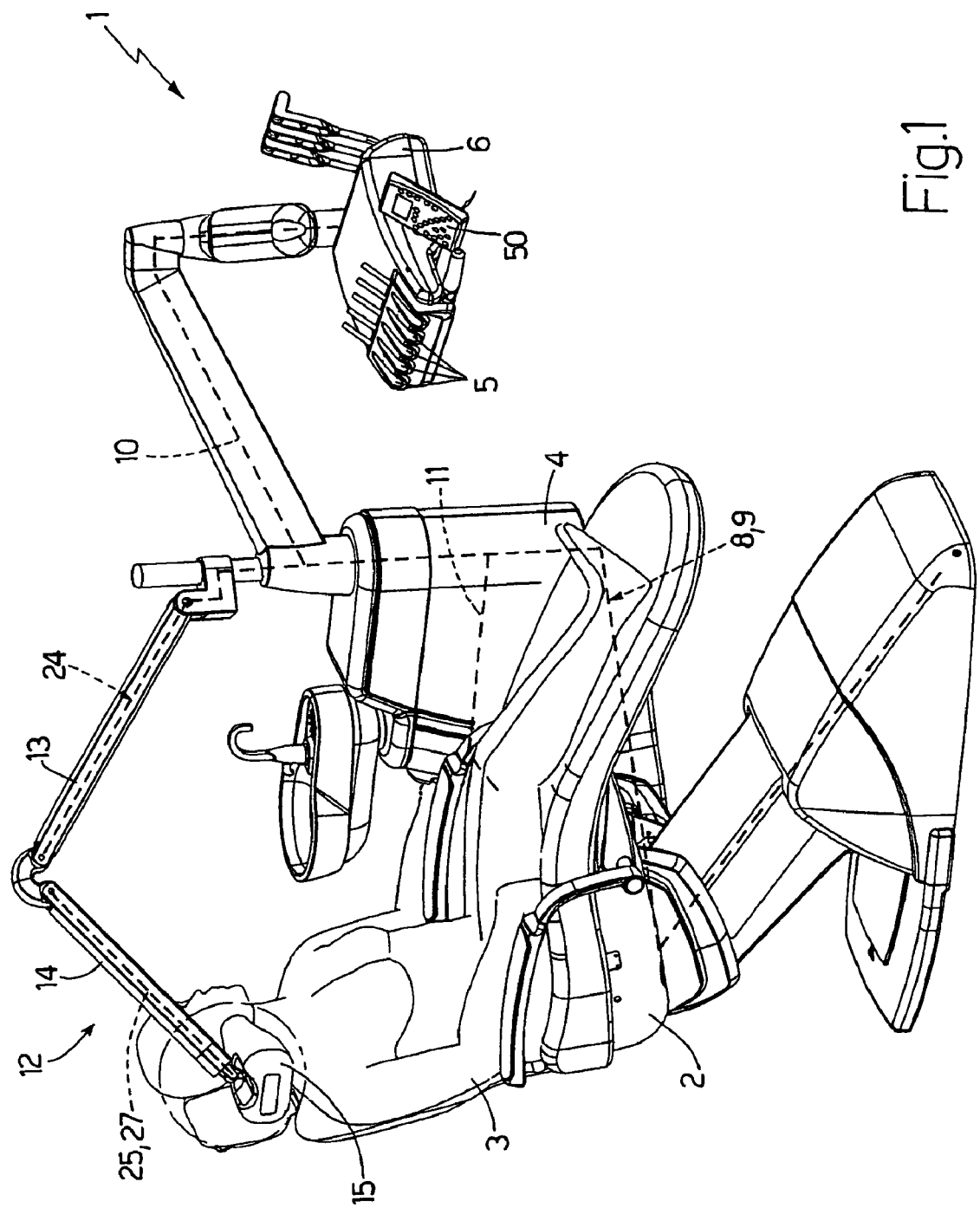
FIG. 1 is a perspective schematic view of a preferred embodiment of the unit of the present invention fitted in a dental chair assembly.

With reference to FIG. 1, it is indicated as a whole by 1 a dental chair assembly comprising a chair 2 of the known type for a patient 3, a vertical upright 4, a plurality of instruments 5 normally used in dental practice and arranged over a supporting table 6 connected to the upright 4, and a bowl 7 fitted over the upright 4 itself.

The upright 4 accommodates inside at least one part of a feeding unit 8, which is adapted to hydraulically and/or pneumatically feed the instruments 5 and the bowl 7, and comprises a hydraulic and/or pneumatic circuit 9, which extends from at least one source (not shown), and comprises, in turn, a first feeding branch 10 for the instruments 5 and a second feeding branch 11 for the bowl 7.

The dental chair assembly 1 is also provided with a unit for acquiring dental radiographic images of the patient 3. The unit 12 comprises two articulated supporting arms 13, 14, of which arm 13 is rotationally coupled, in the case in point, to the upright 4 and the arm 14 is rotationally coupled to the arm 13 and supports, at its free end, an x-ray head 15.

Figure 2:
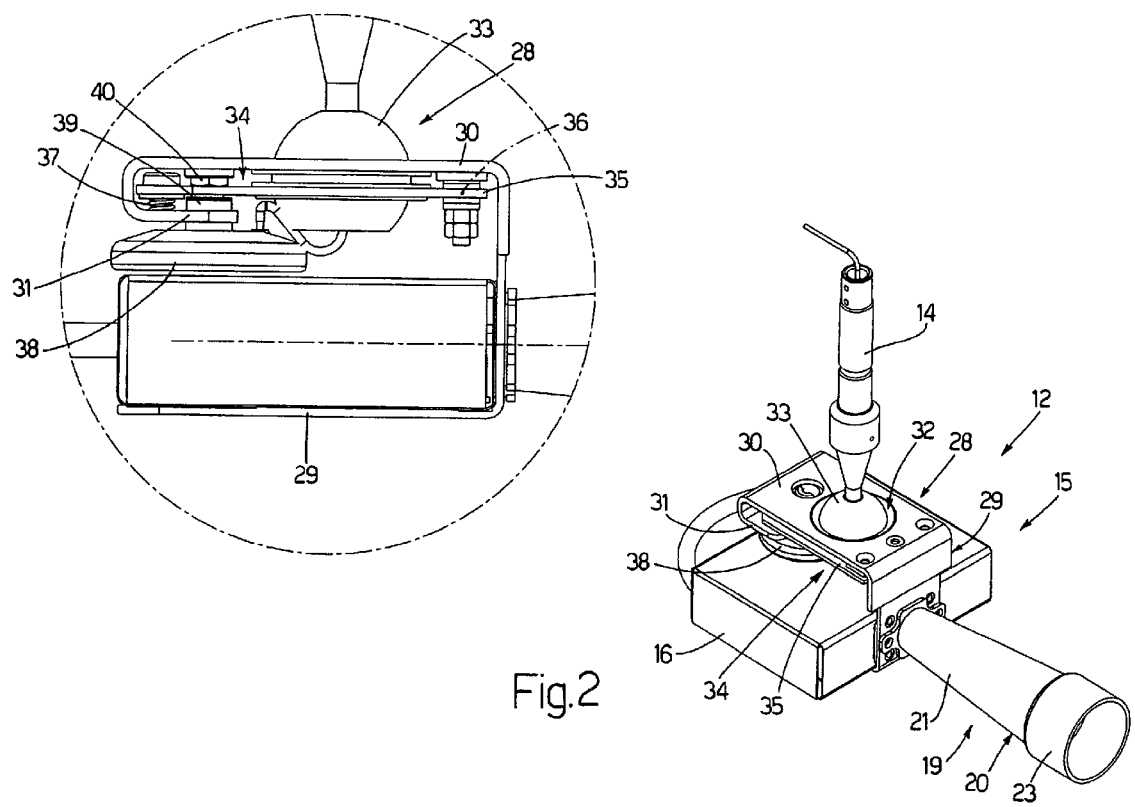
FIG. 2 is a schematic perspective view, with magnified parts and parts removed for clarity, of a detail of the unit in FIG. 1.
Figure 3:
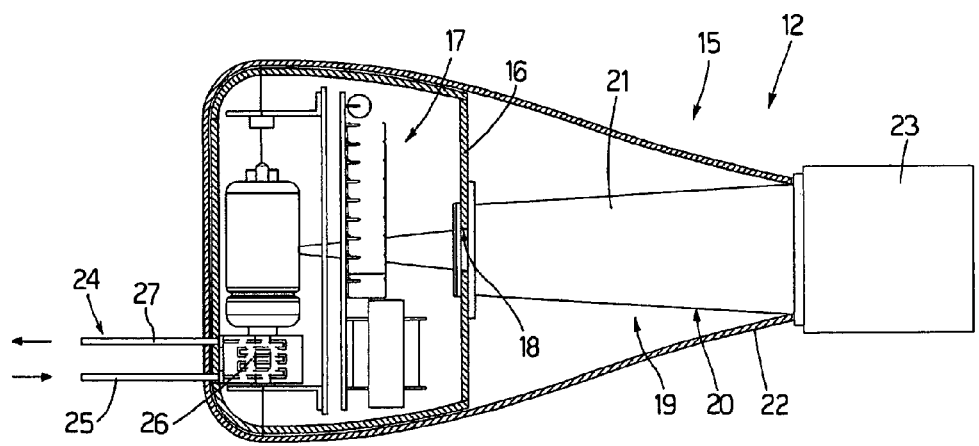
FIG. 3 is a lateral schematic view, with parts in section, of the detail in FIG. 2.

As shown in FIGS. 2 and 3, the x-ray head 15 comprises an inner container 16, which accommodates inside an x-ray generating assembly 17 of the known type, and presents a window 18 made through the container 16 for the output of x-rays from the container 16 itself. The assembly 17 is submerged in a certain amount of dielectric oil contained inside the container 16 and adapted both to electrically isolate the assembly 17, and to dissipate part of the heat generated by the assembly 17 itself.

The x-ray head 15 also comprises an optical assembly 19 of the known type for collimating the x-rays generated by the assembly 17. The assembly 19 is fitted outside the container 16, and comprises an optical element 20 of elongated shape which comprises, in turn, a first substantially truncated cone shaped section 21, which is fastened to the container 16 at the window 18, and is accommodated, along with the container 16 itself, inside an external casing 22, and an essentially cylindrical second section 23 protruding from the casing 22 itself.

Finally, with reference to FIGS. 1 and 3, the x-ray head 15 is provided with a cooling circuit 24, which defines a third branch of the circuit 9, and comprises an input conduit 25, which extends along and inside the arms 13, 14, and also extends through the outer casing 22 and the inner container 16 for supplying a cooling fluid, air or water in the case in point, to a heat exchanger 26 associated to the generating assembly 17. In the case in point, the circuit 24 is a closed loop circuit also comprising an output conduit 27, which extends through the outer casing 22 and the inner container 16, and also extends along and through the arms 13, 14 to supply the cooling fluid from the exchanger 26 outside the x-ray head 15 and again to the mentioned source (not shown).

With reference to that set forth above it is appropriate to specify that, according to a variant not shown, the source of the cooling fluid may be independent and different from the source (not shown) of the unit 8 and the circuit 24 may be an open circuit, whose output conduit 27 directly communicates with the outside environment.

The presence of the circuit 24 allows to reduce the amount of dielectric oil contained inside the container 16, to reduce the weight of the x-ray head 15 and, therefore, of the supporting arms 13, 14, and to simplify the gaskets and the sealing members of the x-ray head 15 itself.

The x-ray head 15 is coupled to the arm 14 by means of a ball joint coupling device 28 comprising a supporting plate 29, which is essentially C-shaped, extends about the container 16, and is fastened to the container 16 so as to present a flat wing 30, which extends parallel to, and at a certain distance from, the container 16, and presents an end edge 31 folded towards the inside between the container 16 and the wing 30 itself. A spherical seat 32 engaged by a spherical member 33 fastened to a free end of the arm 14 is made through the wing 30.

The member 33 is locked in a determined angular position inside the seat 32 by a locking device 34 comprising a flat annular plate 35, which is arranged between the wing 30 and the container 16, extends about the member 33 and between the wing 30 and the edge 31, and is rotationally coupled to the plate 29 to oscillate, with respect to the plate 29 itself, about a fulcrum axis 36 substantially parallel to the wing 30.

The plate 35 is normally maintained in a locking position (not shown) of the member 33 inside the seat 32 by a spring 37, which is arranged between the edge 31 and the plate 35, and is adapted to shift the plate 35 about the axis 36 (clockwise in FIG. 2) and in contact with the wing 30 so as to lock the member 33 inside the seat 32.

The plate 35 is movable from its locking position to a releasing position (FIG. 2), in which the plate 35 is arranged substantially parallel to the wing 30 to release the member 33, under the bias of an actuating cylinder 38, which is fastened to the edge 31, and presents an output rod 39, which extends through the edge 31 and the plate 35, and carries a bolted fastening nut 40 adapted to engage the plate 35 on opposite side with respect to the spring 37 to shift the plate 35 itself about the axis 36 against the bias of the spring 37 (anticlockwise in FIG. 2).

Figure 4:
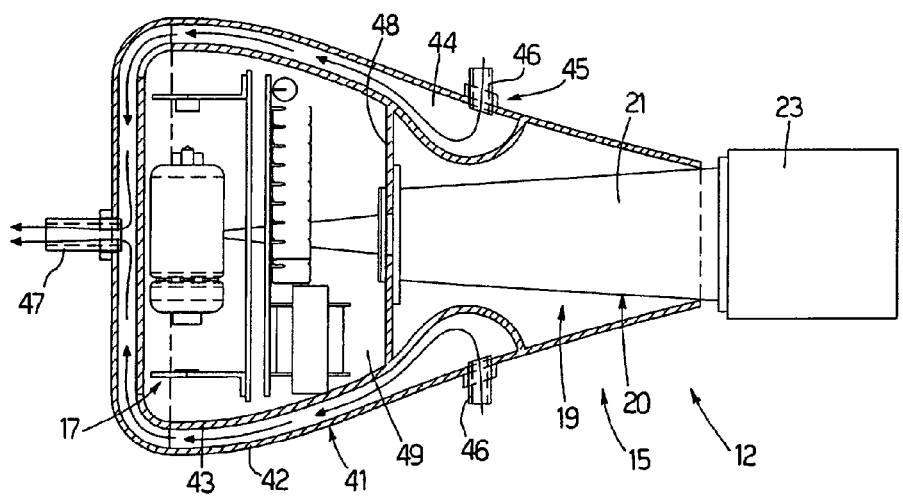
FIG. 4 is a lateral schematic view, with parts in section, of a variant of the detail in FIGS. 2 and 3.

The variant shown in FIG. 4 differs from that shown in FIG. 3 in that, here, the inner container 16 and the outer casing 22 are eliminated and replaced by a casing 41 comprising an outer wall 42 and an inner wall 43 shaped and connected together to delimit a gap 44, which defines part of a cooling circuit 45 of the generating assembly 17, and is connected, in the case in point, to two input conduits 46 of the cooling fluid in the gap 44 similar to the conduit 25 and with an output conduit 47 of the cooling fluid from the gap 44 similar to conduit 27. The casing 41 is also provided with a further inner wall 48 adapted to delimit along with the wall 43, a chamber 49 for accommodating the generating assembly 17 entirely similar to container 16.

According to variants not shown:

container 16 is eliminated and replaced with a container presenting a gap entirely similar to gap 44;

the dielectric oil contained in the container 16 is eliminated and replaced, for example, with a filling resin and part of the cooling circuit 24 is made through the filling resin itself; and cooling circuit 24 is eliminated and replaced by a cooling fan.

With reference to FIG. 1, the operation of the unit 12 is controlled by a control keypad 50 attached, in the case in point, to the supporting table 6 for the instruments 5 and previously used for selecting the operating parameters of the instruments 5 and of the chair 2.

The buttons of the keypad 50 allow to select the operating parameters of the unit 12, such as, for example, the type of tooth to be x-rayed, the patient's build and the exposure time.

The keypad 50 is also provided with a display to display, for example, the selected operating parameters, the radiographic image and a low resolution preview of the radiographic image itself.

According to a variant not shown, the unit 12 is fastened to a supporting wall, in the case in point a wall of the dental surgery.

The invention claimed is:

1. A unit for acquiring dental radiographic images of a patient comprising: an x-ray head, a supporting arm of the x-ray head, coupling means of the x-ray head to the supporting arm, wherein said coupling means comprise a ball joint comprising a spherical member carried by said supporting arm and x-ray head and a housing seat of the spherical member; and a locking device for locking the ball joint in a determined angular position, the locking device comprising at least one locking member mobile between a locking position of the spherical member inside said housing seat and a releasing position, and actuating means for shifting the locking member between said locking and releasing positions; wherein the ball joint comprises a first plate provided with said housing seat; the locking device comprising a second plate, which extends about the spherical member, defines said locking member, and is rotationally coupled to the first plate to oscillate, with respect to the first plate, between said locking and releasing positions; and the actuating means comprising an actuating cylinder for shifting the second plate from the locking position to the releasing position.

2. A unit according to claim 1, wherein said actuating means further comprise a spring for normally maintaining the second plate in said locking position.

3. A dental chair assembly comprising: a chair for a patient; and a unit for acquiring dental radiographic images of the patient, said unit comprising: an x-ray head, a supporting arm of the x-ray head, coupling means of the x-ray head to the supporting arm wherein said coupling means comprises a ball joint comprising a spherical member carried by said supporting arm and x-ray head and a housing seat of the spherical member; and a locking device for locking the ball joint in a determined angular position, the locking device comprising at least one locking member mobile between a locking position of the spherical member inside said housing seat and a releasing position, and actuating means for shifting the locking member between said locking and releasing positions; wherein the ball joint comprises a first plate provided with said housing seat; the locking device comprising a second plate, which extends about the spherical member, defines said locking member, and is rotationally coupled to the first plate to oscillate, with respect to the first plate, between said locking and releasing positions; and the actuating means comprising an actuating cylinder for shifting the second plate from the locking position to the releasing position.

* * * * *